United States Patent [19]
Alexander et al.

[11] Patent Number: 5,631,384
[45] Date of Patent: May 20, 1997

[54] ARENO [E]INDOLS, PREPARATION METHOD AND APPLICATION AS INTERMEDIATES IN THE SYNTHESIS OF PRODUCTS WITH ANTITUMORAL ACTIVITY

[75] Inventors: Koen Alexander, Amsterdam, Netherlands; Jose Delamano Garcia, Villagarcia de Arosa, Spain; Benedikt Sas, Turnhout, Belgium; Gabriel Tojo Suarez, Santiago de Compostela; Dolores Garcia Gravalos, Madrid, both of Spain

[73] Assignee: Pharma-Mar, S.A.-Pharmar, Colmenar Viejo, Spain

[21] Appl. No.: 674,863

[22] Filed: Jul. 3, 1996

Related U.S. Application Data

[62] Division of Ser. No. 252,658, filed as PCT/ES93/00078 Sep. 22, 1993, Pat. No. 5,571,927.

[30] Foreign Application Priority Data

Sep. 22, 1992 [ES] Spain ..................................... 9201894

[51] Int. Cl.$^6$ ...................... C07D 487/02; C07D 209/56
[52] U.S. Cl. ............................................. 548/433; 548/429
[58] Field of Search ..................................... 548/429, 433

[56] References Cited

PUBLICATIONS

Paul Carter, Steven Fitzjohn, Serge Halazy, and Philip Magnus, "Studies on the Synthesis of the Antitumor Agent CC–1065 Synthesis of PDE I and PDE II, Inhibitors of Cyclic Adenosine–3',5'–monophosphate Phosphodiesterase using the 3,3'–Bipyrrole Strategy", *J. Am. Chem. Soc.* (1987), 109, 2711–2717.

Frank B. Mallory and Clelia W. Mallory, "Photocyclization of Stilbenes and Related Molecules", *Organic Reactions*, vol. 30, (1984) pp. 266–313.

Viresh H. Rawal, Robert J. Jones and Michael P. Cava, "Palladium Mediated Dehydrogenation in the Photochemical Cyclization of Heterocyclic Analogs of Stilbene", *Tetrahedron Letters*, vol. 26, No. 20, (1985) pp. 2423–2426.

Viresh H. Rawal, Robert J. Jones and Michael P. Cava, "Photocyclization Strategy for the Synthesis of Antitumor Agent CC–1065: Synthesis of Dideoxy PDE–I and PDE–II. Synthesis of Thiophene and Furan Analogues of Dideoxy PDE–I and PDE–II", *J. Org. Chem.*, 1987, 52, 19–28, (1987).

Kevin J. Drost and Michael P. Cava, "A Photochemically Based Synthesis of the Benzannelated Analogue of the CC–1065 A Unit", *J. Org. Chem.*, (1991), 56, 2240–2244.

Viresh H. Rawal, Robert J. Jones, and Michael P. Cava, "Review of Synthetic Studies Toward CC–1065, PDE–I, and PDE–II$^+$", *Heterocycles*, vol. 25, (1987).

*Primary Examiner*—Jacqueline Haley
*Attorney, Agent, or Firm*—Darby & Darby

[57] ABSTRACT

The compounds (I) are useful as intermediates in the synthesis of hexahydroareno(e)cyclopropa(c)indol-4-ones with antitumoral activity.

4 Claims, No Drawings

ARENO [E]INDOLS, PREPARATION METHOD AND APPLICATION AS INTERMEDIATES IN THE SYNTHESIS OF PRODUCTS WITH ANTITUMORAL ACTIVITY

This is a division, of application Ser. No. 08/252,658, filed as PCT/ES93/00078 Sep. 22, 1993 now U.S. Pat. No. 5,571,927.

TECHNICAL FIELD OF THE INVENTION

The present invention is comprised in the technical field of the production of compounds with antitumoral activity.

Specifically, the present invention refers to the obtainment of new areno indols, useful in the synthesis of hexahydroareno[e]cidopropa[c]indol-4-ones with antitumoral properties.

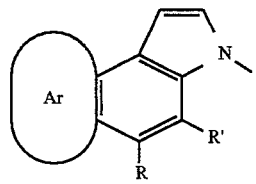

On the other hand, the areno[e]indols (III) are intermediates useful for preparing hexahydroareno[e]cyclopropa[c]indol-4-ones (IV.) These indolones have a great pharmaceutical interest as they contain the structural unity of cyclopropa[c]indol-4-one which, among others D. L. Boger et al. in J. Am. Chem. Soc., 113, 2779 (1991) have proven that it is responsible for the antitumoral activity of the CC-1065 agent (V) and synthesis analogues of the same.

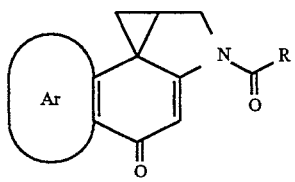

(IV)

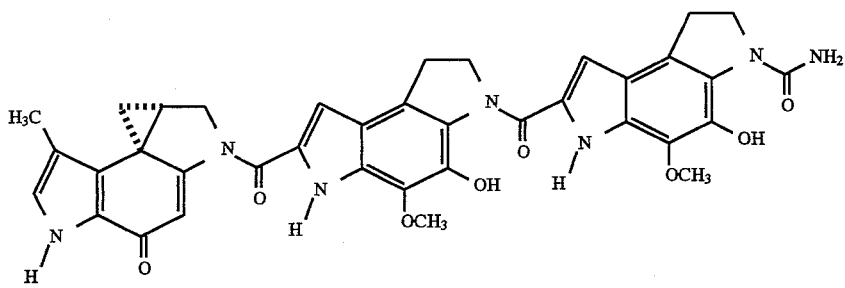

CC-1065: (V)

PRIOR ART OF THE INVENTION

Obtaining phenantrenes by oxidative photochemical cycling of stilbenes is a synthetic method largely used as can be seen in the review of F. B. Mallory and C. W. Mallory in Organic Reactions, Wiley: New York, 1984; Vol. 30, page 1. The analogous reaction of oxidative photocycling of 1-aryl-2-pyrrilethylenes (II) to produce areno[e]indols (III) is less described in the bibliography, in spite of its unquestionable potential. The reason is that this reaction tends to give very small yields and is highly dependent on the substrate. This small yield is often due to the oxidative decomposition in the reaction medium of the 1-aryl-2-pyrrilethylenes (II) as starting products. A solution to this problem consists of the use of carefully studied reaction conditions to give the best yields in a given substrate. Hence, for example, M. P. Cava et al. in J. Org. Chem., 56, 2240 (1991) and cited references have carried out these oxidative cyclings on some 1-aryl-2-pyrrilethylenes (II), irradiating them with ultraviolet light in the presence of palladium on carbon, silica-gel, triethylamine and p-nitrobenzoic acid in acetonitrile to reflux and an inert atmosphere, with very good yields. These good yields are obtained however as a result of a laborious search for reaction conditions which end up being little versatile; furthermore, these conditions may end up to be technically complex to use.

The object of the present invention is to solve the problem raised in the preparation of areno[e]indols (III) by photochemical irradiation in the presence of 1-aryl-2-pyrrilethylene oxidants (II.)

The problems associated with the photochemical cycling of 1-aryl-2-pyrrilethylenes (II) are solved in this invention by preparing compounds of general structure (II) wherein the double central bond is substituted by an arylsulfonyl group. This group acts by drawing out charge and therefore stabilizing the 1-aryl-2-pyrrilethylene to which it is linked against undesired oxidations, which allows easy photocycling thereof leading to an areno[e]indol substituted with an arylsulfonyl group, that can be easily eliminated, if desired, by using a reducing agent capable of breaking the carbon sulfur bond.

DETAILED DESCRIPTION OF THE INVENTION

Just as is stated in the title hereof, the present invention refers to new areno[e]indols, preparation method and application thereof as intermediates in the synthesis of products with antitumoral activity. Said new areno[e]indols have the general formula (I):

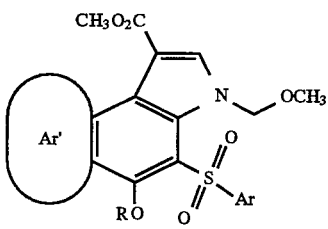

wherein —Ar represents phenyl or substituted phenyl, Ar' represents a condensed radical of formula:

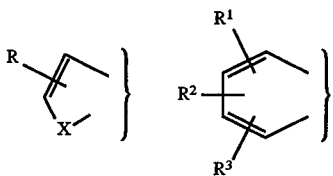

wherein R, $R^1$, $R^2$, $R^3$ may represent hydrogen, halogen, a linear or branched alkyl, alkenyl or alkynyl radical, a formyl, acyl, carboxy, akoxycarbonyl, aminocarbonyl, alkylaminocarbonyl, dialkylaminocarbonyl, cyano, hydroxy, alkoxy, amino, alkylamino, dialkylamino, acylamino or nitro radical and X represents oxygen, sulfur or a substituted or unsubstituted nitrogen and —R represents an acyl group with 2 to 5 linear or branched chain carbon atoms.

In order to obtain the compounds of formula (I) one starts with a methyl 2-arylsulfinylmethyl-N-methoxymethyl-4-pyrrolcarboxylate of general formula (VI):

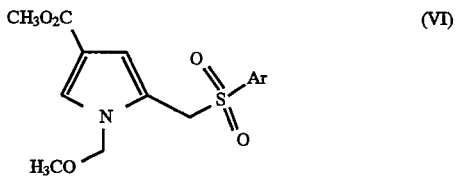

wherein Ar has the meaning given above.

These compounds of formula (VI) can be prepared, in turn, starting with methyl 2-formyl-pyrrolcarboxylate, a compound that is easily obtained by using the process described by H. J. Anderson, C. E. Loader and A. Foster in Cam. J. Chem., 58, 2527 (1980.)

The treatment of methyl 2-formyl-4-pyrrolcarboylate with chloromethyl ethyl ether in the presence of a base and an adequate organic solvent results in methyl 2-formyl-N-methoxymethyl-4-pyrrolcarboxylate. The base used is an alkoxide, a tertiary amine, an alkaline amide or an organolytic compound: the organic solvent is an aprotic dipolar solvent, an ether or a hydrocarboned solvent: the reaction time is between 1 and 40 hours and the temperature between −10° and 50° C.

The reduction of methyl 2-formyl-N-methoxymethyl-4-pyrrolcarboxylate with a metal hydride in an organic solvent leads to the formation of methyl 2-hydroxymethyl-N-methoxymethyl-4-pyrrolcarboxylate. Normally the preferred metal hydride is boron hydride and the organic solvent is an alcohol with a low molecular weight such as methanol or ethanol. The reaction temperature is generally between 0° and 40° C. and the time between 0.5 and 3 hours.

The treatment of methyl 2-hydroxymethyl-N-methoxymethyl4-pyrrolcarboxylate with a substituted or unsubstituted benzenesulfinate in an acid medium gives rise to methyl 2-aryl-sulfinylmetho-N-methoxymethyl-4-pyrrolcarboxylate of general formula (VI) indicated above. In the same manner as the benzenesulfinate, 1-toluenesulfinate can be used its counter-ion ion being a metallic cation, usually a sodium cation. The acid medium tends to be determined by an organic acid that is normally used as the solvent, for example, formic acid. The reaction temperature is normally between 0° and 50° C. and the time between 0.5 and 3 days.

The first step of the process of the invention includes reacting methyl 2-arylsulfinilmetyl-N-methoxymethyl-4-pyrrolcarboxylate (VI) with a strong base in an inert solvent and then with an aromatic aldehyde, obtaining as a product of the reaction the compounds methyl 2-(2-aryl-1-arylsulfonil-2-hydroxyethyl)-N-methoxymethylpyrrol-4-carboxylate compounds of general formula:

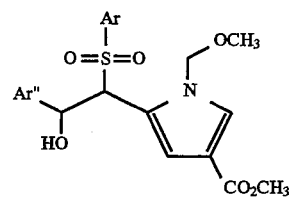

wherein Ar" represents an aryl, phenyl, pyrrolyl, furyl or thiophenyl group substituted up to three times by any of the above mentioned radicals R, $R^1$, $R^2$, and $R^3$ and Ar has the meaning given above.

The strong base used to obtain the compound of formula (VII) can be alkaline amide, an alkyl-lithium or an aryl-lithium, preferably lithium diisopropylamide; the solvent has to be an inert solvent such as dialkyl ether, 1,4-dioxane or tetrahydrofuran, preferably tetrahydrofuran, and the aldehyde an aromatic aldehyde, such as methyl 2-formyl-N-methoxymethylpyrrol-4-carboxylate, 4-methoxybenzaldehyde or 3,4,5-trimethoxybenzaldehyde.

The compounds of formula (VII) obtained are oxidized in an inert solvent to give the corresponding ketone of general formula:

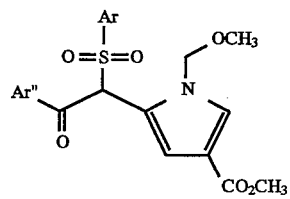

wherein —Ar and —Ar" have the above cited meaning.

The oxidant used is 2,3-dicyano-5,6-dichloro-p-benzoquinone and the inert solvent benzene, toluene, xylene, 1,4-dioxane or chlorobenzene.

The ketone of general formula (VIII) is subjected to acylation by treating it with a suitable base in an inert solvent and then with an acyl chloride as an acylating agent, obtaining the acylated derivate of general formula:

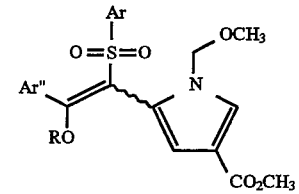

wherein Ar, Ar" and R have the meaning given above.

The base used can be an amine, an alkaline amide, an alkyl-lithium or an aryl-lithium, preferably triethylamine; the inert solvent may be chloroform, dichloromethane or 1,2-dichloroethane and the acylating agent a chloride of an acid having 2 to 5 linear or branched chain carbon atoms, preferably acetyl chloride.

The compound of formula (IX) is subjected to a photochemical cycling process in an organic solvent, preferably an alcohol with a low molecular weight such as methanol or ethanol, in the presence of an oxidant, such as oxygen associated catalytic iodine, and under ultraviolet irradiation.

The compound obtained by this photochemical cycling process from the acylated derivative of formula (IX) is a compound of general formula (I), an intermediary product in the synthesis of compounds with antitumoral activity.

EMBODIMENTS OF THE INVENTION

The present invention is illustrated with the following example, that are not intended to limit at all the scope of the applicability thereof.

In order to describe the physical data of the synthesized compounds the following abbreviations are used:

m.p.: melting point

IR: infrared

UV: ultraviolet $^1$H-NMR: nuclear magnetic resonance

S: singlet d: doblet t: triplet m: multiplet

J: coupling constant

MS: mass spectrum ei: electronic impact

FAB: fast atom bombardment $M^+$: molecular ion

ø: diameter

TS: tosyl-p-toluenesulfonyl

EXAMPLE OF PREPARATION

Preparation of methyl N-methoxymethyl-2-tosylmethyl-4-pyrrolcarboxylate

Step 1: Preparation of methyl 2-formyl-N-methoxymethyl-4-pyrrolcarboxylate

A solution of 5.995 g of methyl 2-formyl-4-pyrrolcarboxylate is prepared in 60 mL of dry N,N-dimethylformamide, in a flask provided with a calcium chloride tube. To this solution magnetically stirred and cooled in an ice/water bath 7.323 g. of potassium tertbutoxide were added. When the addition was ended, the reaction is left to room temperature and the stirring is maintained for 1.75 hours, after which the reaction is cooled again in an ice/water bath and 6 mL of chloromethyl ethyl ther are added slowly. After the addition is finished the reaction is left to room temperature and the stirring is maintained for 18 hours. Thereafter, by fine layer chromatography analysis the existence of the starting product is tested, so that, by repeating the same process used above, 1.864 g. of potassium tert-butoxide and 1.5 mL of chloromethyl methyl ether were added, leaving the stirring at room temperature for 16 more hours.

The preparation is carried out by adding water and extraction with ethyl acetate, followed by drying the organic phase with sodium sulfate and elimination of the solvent in a steam rotator, resulting in an oil that is purified by silica gel column chromatography (25×3 cm ø), by elution with dichloromethanol/ethyl acetate (20:1.) 6.817 g. of protected pyrrol are obtained.

Yield: 88% m.p.: 65°–66° C. (petroleum ether:diethyl ether)

IR(KBr, maximum δ): 1670, 1705, 2950, 3115 cm$^{-1}$

UV (ethanol, maximum λ): 220, 278 nm.

$^1$H-NMR (CDCl$_3$): 3.34 (s, 3H, ArCH$_2$OCH$_3$), 3.85 (s, 3H, ArCO$_2$CH$_3$), 5.67 (s, 2H, ArCH$_2$OCH$_3$), 7.39 (d. 1H, J=1.6 Hz, ArH), 7.69 (s wide, 1H, ArH), 9.62 (d, 1H, J=0.8 Hz, ArCHO) ppm.

MS (e.i., m/e, %): 197 (M$^+$, 29) 182 (M$^+$—CH$_3$, 100), 166 (M$^+$ —OCH$_3$, 28), 154 (M$^+$—CH$_3$CO, 23.)

Elemental analysis for C$_9$H$_{11}$NO$_4$:

Calculated: % C=54.77; % H=5.62; % N=7.10

Found: % C=55.04; % H=5.65; % N=6.95

Step 2: Preparation of methyl 2-hydroxymethyl-N-methoxymethyl-4-pyrrolcarboxylate 165 mg. NaBH$_4$ are added to a magnetically stirred solution cooled in an ice/water bath of 515 mg. of methyl 2-formyl-N-methoxymethyl-4-pyrrolcarboxylate in 8 mL of dry methanol, in a flask provided with a calcium chloride tube. After the addition has been ended, stirring is maintained for 1.5 hours.

Addition of water to the reaction mixture followed by elimination of the methanol in the steam rotor, extraction with ethyl acetate, drying the organic phase with sodium sulfate and elimination of the solvent in the steam rotor, gives rise to an oil, which is purified by silica gel column chromatography (15×2 cm ø), by elution with dichloromethane/ethyl acetate (5:1), whereby 507 mg of the desired alcohol are obtained.

Yield: 98% m.p.: 56°–57° C. (ethyl acetate:hexane)

IR (KRr, maximum δ): 1710, 2950, 3120, 3400 wide cm$^{-1}$

UV ethanol, maximum λ): 208, 225, 260 $_{shoulder}$ nm $^1$H-NMR (CDCl$_3$): 3.29 (s, 3H, ArCH$_2$OCH$_3$), 3.80 (s, 3H, ArCO$_2$CH$_3$), 4.61 (s, 2H, ArCH$_2$OH). 5.28 (s, 2H, ArCH$_2$OCH$_3$), 6.60 (d, 1H, J=1.6 Hz, ArH), 7.40 (d, 1H, J=1.7 Hz, ArH) ppm.

MS (e.i., m/s, %): 199 (M$^+$, 182 (M$^+$ —OH, 3), 168 (M$^+$ —OCH$_3$, 13) 45 (CH$_3$OCH$_2$+, 100).

Elementary analysis for C$_9$H$_{13}$NO$_4$:

Calculated: % C=54.26; % H=6.57; % N=7.03

Found: % C=53.91; % H=6.82; % N=6.95

Step 3: Preparation of methyl N-methoxymethyl-2-tosylmethyl-4-pyrrolcarboxylate

A solution of 438 mg. methyl 2-hydroxymethyl-N-methoxymethyl-4-pyrrolcarboxylate and 1.881 g. of sodium p-toluenesulfinate in 5 mL of aqueous 85% formic acid is stirred at room temperature for 23 hours.

Addition of water to the reaction mixture, followed by extraction with dichloromethane, drying of the organic phase with sodium sulfate and elimination of the solvent in the steam rotator, leads to a solid that is purified by means of a silica gel column (15×1.5 cm, ø), elution with dichloromethane:ethyl acetate (20:1), whereby 702 mg. of sulfone are obtained.

Yield: 95% m.p.: 104°–105° C. (ethyl acetate: petroleum ether)

IR (KBR, maximum δ): 1705. 2940, 3120 cm$^{-1}$

IV ethanol, maximum λ): 202, 208, 226 nm $^1$H-NMR (CDCl$_3$): 2.44 (s, 3H, ARCH$_3$), 3.17 (s, 3H, ArCH$_2$OCH$_3$), 3.77 (s. 3H, ArCO$_2$CH$_3$), 4.42 (s, 2H, ArCH$_2$Ts), 5.27 (s, 2H, ArCH$_2$OCH$_3$). 6.30 (d, 1H, J=1.3

Hz, ArH), 7.30 (d, 2H, J=8.2 Hz, ArH), 7.38 (d, 1H, J=1.7 Hz, ArH), 7.57 (d, 2H, J=8.2 Hz, ArH) ppm.

MS (e.i., m/s, %), 337 (M$^{+\cdot}$, 0.3) 306 (M$^{+\cdot}$ —OCH$_3$, 3), 1.82 (M$^{+\cdot}$ —SO$_2$(C$_6$H$_4$)CH$_3$, 100).

Elementary analysis for C$_{16}$H$_{19}$MO$_5$S:

Calculated: % C=56.96: % H=5.67: % N=4.15

Found: % C=56.83: % H=5.80; % N=3.86

EXAMPLE 1

1) Methyl 2-[2-hydroxy-2-(4-methoxycarbonyl-N-methoxymethyl-2-pyrryl)-1-tosylethyl]-N-methoxymethyl-4-pyrrolcarboxylate A solution of lithium diisoproplyamide is prepared by adding 0.8 mL of a 2.7M solution of n-butyl-lithium in hexane on a solution of 0.31 mL of diisopropylamine in 20 mL of tetrahydrofuran. 600 mg. of methyl N-methoxymethyl-2-tosylmethyl-4-pyrrolcarboxylate are added to the solution of lithium diisopropylamide stirred magnetically and cooled to −75° C. The temperature of the resulting suspension is left to rise to −40° C. for 1.25 hours and on the generated red soluion 351 mg. of methyl 2-formyl-N-methoxymethyl-4-pyrrolcarboxylate are added. The temperature of the reaction mixture is left to rise to −15° C. for 2 hours and 5 mL of hydrochloric acid 10% are added.

Addtion of 20 mL of brine, followed by extraction with diethyl ether, drying of the organic phase with sodium sulfate and elimination of the solvent in a steam rotator, leads to a solid residue that is purified on silica gel column chromatography (18×2 cm ∅), using an elution gradient of dichloromethane/ethyl acetate increasing the proportion of ethyl acetate from 15 to 25%. 921 mg. of the condensation product is obtained as a sole diastereoisomer.

Yield: 97% m.p.: 180°–181° C. (ethyl acetate)

IR (KBr, maximum γ): 1688, 1715, 2950, 3120, 3460 cm$^{-1}$

UV (ethanol, maximum λ): 205, 225 $_{shoulder}$, 255 $_{shoulder}$ nm $^1$H-NMR (CDCl$_3$): 2.40 (S, 3H, ARCH$_3$), 3.08 (s, 3H, ArCH$_2$OCH$_3$), 3.17 (s, 3H, ArCH$_2$OCH$_3$), 3.67 (s, 3H, ArCO$_2$CH$_3$) 3.71 (s, 3H, ArCO$_2$CH$_3$), 4.06 (d, 1H, J=3.7 Hz, ArCH(R)OH) 4.70 (d, 1H, J=11.4 Hz, ArCH$_2$OCH$_3$), 5.09 (m, 2H, ArCH$_2$OCH$_3$ and ArCH(Ts)R), 5.36 (d, 1H, J=11.5 Hz, ArCH$_2$OCH$_3$), 5.37 (d, 1H, J=10.7 Hz, ArCH$_2$OCH$_3$), 5.54 (dd, 1H, J=2.6 and 10.4 Hz, ArCH(OH)R), 6.42 (d, 1H, J=1.3 Hz, ArH), 6.49 (d, 1H, J=1.5 Hz, ArH), 7.18 (m, 2H, ArH), 7.25 (d, 2H, J=7.9 Hz, ArH) 7.57 (d, 2H, J=8.3 Hz, ArH) ppm.

MS (FAB m/s %): 535 (M+1H$_2$O, 29) 503 (M+1—CH$_3$OH, 28), 489 (M+1—CH$_3$OCH$_3$,6), 379 (M+1—CH$_3$(C$_6$H$_4$)SO$_2$H, 4), 362 M+1+H$_2$O—CH$_3$(C$_6$H$_4$)SO$_2$, 100), 348 (M+1—CH$_3$(C$_6$H$_4$)SO$_2$H—OCH$_3$, 21), 333 (M+1—CH$_3$(C$_6$H$_4$)SO$_2$H—CH$_3$OCH$_3$, 9) 315 (M+1—CH$_3$(C$_6$H$_4$)SO$_2$H—CH$_3$OCH$_3$—H$_2$O, 61) 182 (ArCH$_2$A, 83).

Elementary analysis for C$_{25}$H$_{30}$N$_2$O$_9$S:

Calculated: % C=56.17; % H=5.66; % N=5.24% S=6.00

Found: % C=55.92; 4 H=5.58; % N=5.22; % S=6,36

2) Methyl 2-[2-hydroxy-2-(4-methoxyphenyl)-1-tosylethyl]-N-methoxymethyl-4-pyrrolcarboxylate A solution of lithium diisopropylamide is prepared by adding 4.21 mL of a 2.4M solution of -n-butyl-lithium in hexanes on a 1.5 mL solution of diisopropylaminde in 100 mL of tetrahydrofuran. 2.9 g. of methyl N-methoxy-2-tosylmethyl-4-pyrrolcarboxylate are added to a solution of lithium diisopropylamide stirred magnetically and cooled to −50° C. 2 hours later 1.06 mL of methoxybenzaldehyde are added on the generated red solution. 1 hour later HCl 10% is added.

Addition of brine, followed by extraction with diethyl ether, drying the organic phase with sodium sulfate and elimination of the solvent in a steam rotator, leads to a dry residue that is purified by silica gel column chromatography (27×3.5 cm ∅), by elution with dichloromethane/ethyl acetate (3:1.) 3.58 g. of the condensation product are obtained as two diastereoeisomers in the ratio of 3:1.

Yield: 88%

IR (film, maximum δ): 1560, 1610, 1710, 2960, 3480 cm$^{-1}$

UV (ethanol, maximum λ): 204, 328 nm $^1$H-NMR (CDCl$_3$): 2.37 (s, ArCH$_3$, minority), 2.40 (s, CH$_2$OCH$_3$, minority) 2.42 (s, ArCH$_3$, majority), 2.50 (s, CH$_2$OCH$_3$, majority), 3.70 (s, CO$_2$CH$_3$, majority+minority), 3.79 (s, ArOCH$_3$, majority+minority), 4.05 (d, J=11.3 Hz, NCH$_2$OCH$_3$, minority), 4.39 (d, J=11.13 Hz, NCH$_2$OCH$_3$, minority). 4.39 (d, J=11.3 Hz, NCH$_2$OCH$_3$ majority), 4.48 (d, J=11.3 Hz, NCH$_2$OCH$_3$, minority) 4.56 (d, J=1.9 Hz, HCOH, minority), 4.75 (d, J=9.8 Hz, HCOH, majority), 4.78 (d, J=11.3 Hz, NCH$_2$OCH$_3$, majority), 5.33 (d, J=9.8 Hz, CHTs, majority), 5.80 (d, J=1.9 Hz, CHTs, minority), 6.61 (d, J=1.4 Hz, ArH, majority), 6.68 (d, J=8.7 Hz, ArH, majority), 6.71 (d, J=8.6 Hz, ArH, minority), 7.00 (d, J=1.4 Hz, ArH, majority+minority), 7.02 (d, J=8.6 Hz, ArH, minority), 7.14 (d, J=8.7 Hz, ArH. majority), 7.27 (d, J=8.3 Hz, ArH, majority), 7.37 (d, J=1.4 Hz, ArH, minority), 7.57 (d, J=8.3 Hz, ArH, majority+minority), 7.64 (d, J=8.3 Hz, ArH, minority)

MS (FAB m/s %): 474 (M+1.7) 476 (M+1—H$_2$O, 63) 442 (M+1—HOCH$_3$, 3) 318 (M+1—TsH,24), 301 (M+1—H$_2$O—TsH, 70), 286 (M+1—HOCH$_3$—TsH, 67) 258 (M+1—HOCH$_3$—TsH—CO, 23.)

Elementary analysis for C$_{24}$H$_{27}$NO$_7$S:

Calculated: % C=60.87: % H - 5.75: % N=2.96

Found: % C=61.32: % H=5.96; % N=2.72

3) Methyl 2-[2-hydroxy-2-(3,4,5-trimethoxyphenyl)-1-tosylethyl]-N-methoxymethyl-4-pyrrolcarboxylate A solution of lithium diisoproplylamide is prepared by adding 4.8 mL of a solution of 2.44M n-butyl-lithium in hexanes on a solution of 1.9 Ml of diisopropylamine in 70 mL of tetrahydrofuran. 3.0 g. of methyl N-methoxymethyl-2-tosylmethyl-4-pyrrolcarboxylate are added to the solution of lithium diisopropylamide stirred magnetically and cooled to −80° C. The resulting suspension is left stirring at −50° C. for 2.3 hours and 1.75 g. of 3,4,5-trimethoxybenzaldehyde are added to the generated red solution. After 1.5 hours of stirring at −50° C. the reaction is cooled to −70° C. and 100 ml. of hydrochloric acid 10% are added.

Extraction with diethyl ether, followed by drying of the organic phase with sodium sulfate and elimination of the solvent in the steam rotator, leads to a solid residue that is purified by recrystallization of dichloromethanecyclohexane, giving a first fraction that is mixed with a second fraction of product, result of concentrating the mother liquors, dissolving the residue in methanol, adding cyclohexane and filtering the resulting precipitate. 3,15 g. of the condensation product are obtained as two two diasteroisomers in the ratio of 3:1.

Yield: 66% m.p. 80°–90° C.

IR (film, maximum δ): 1590, 1710, 2950, 3000. 3470 cm$^{-1}$

UV (ethanol, maximum λ): 282 nm $^{H}$-NMR (CDCl$_3$): 2.34 (d, J=1.3 Hz, ArCH$_3$ minority), 2.40 (t, J=1.5 Hz, ArCH$_3$ majority), 3.85–3.65 (m, ArOCH$_3$+ CO$_2$CH$_3$+CH$_2$OCH$_3$, majority+minority), 3.98 (d, J=1.7 Hz, NCH$_2$OCH$_3$ minoirty). 4.43 (d, J=10.8 Hz, NCH$_2$OCH$_3$ majority), 4.45 (d, J=1.7 Hz, NCH$_2$OCH$_3$ minority), 4.76–4.62 (m, HCOH+HCTs, majority+minority), 5.32 (d, J=9.5 Hz, NCH$_2$OCH$_3$ majority), 5.85 (s, OH) 633 (d, J=1.1 Hz, ArH minority), 6.44 (d, J=1.3 Hz, ArH majority), 6.73 (s, ArH majority), 6.98 (t, J=1.6 Hz, ArH majority), 7.08 (t, J=1.6 Hz, ArH minority), 7.24 (d, ArH minoirty), 7.25 (dd, ArH majority), 7.34 (s, ArH minority), 7.57 (dd, J=1.5 and 8.4 Hz, ArH majority), 7.61 (d, J=6.9 Hz, ArH minority) ppm.

EXAMPLE 2

1) Methyl 2-[2-(4-methoxycarbonyl-N-methoxymethyl-2-pirryl)-2-oxo-1-tosylethyl]-N-,ethoxymethyl-4-pyrrolcarboxylate A mixture of 2.35 g. of methyl 2-[2-hydroxy-2-(4-methoxycarbonyl-N-methoxymethyl-2-pyrril)-1-tosylethyl]-N-methoxymethyl-pyrrolcarboxylate and 2.51 g. of 2,3-dicyano-5,6-dichloro-p-benzoquinone in 25 mL of dry benzene is heated to reflux under argon for 24 hours.

Addition of 100 mL of a saturated solution of Na$_2$S$_2$O$_5$, followed by extraction with dichloromethane, washing the organic solution with a saturated Na$_2$S$_2$O$_5$ solution, drying with sodium sulfate and concentration of the same, gives rise to an oil that is purified by silica gel column chromatography (20×2 cm ø), by elution with ethyl acetate hexane (1:1) to give rise to 2.20 g. of the desired ketone.

Yield: 92% m.p.: 58°–60° C. (ethyl acetate-hexane)

IR (KBr, maximum δ): 1670, 1718, 2950, 3120 cm$^{-1}$

UV (ethanol, maximum λ): 208, 222 $_{shoulder}$, 293 nm $^1$H-NMR (CDCl$_3$): 2.39 (s, 3H, ArCH$_3$); 3.27 (s, 6H, ArCH$_2$OCH$_3$), 3.71 (s, 3H, ArCO$_2$CH$_3$), 3.79 (s, 3H, ArCO$_2$CH$_3$), 4.92 (d, 1H, J=11.1 Hz, ArCH$_2$OCH$_3$), 5.58 (d, 1H, J=10.2 Hz, ArCH$_2$OCH$_3$), 5.61 (d, 1H, J=10.2 Hz, ArCH$_2$OCH$_3$), 6.04 (d, 1H, J=11.1 Hz, ArCH$_2$OCH$_3$), 6.27 (s, 1H, ArCH (Ts)R), 6.47 (d, 1H, J=1.7 Hz, ArH), 7.22 (d, 2H, J=8.2 Hz, ArH), 7.42 (d, 1H, J=1.8 Hz, ArH), 7.50 (d, 2H, J=8.3 Hz, ArH), 7.59 (d, 1H, J=1.7 Hz, ArH), 7.64 (d, 1H, J=1.7 Hz, ArH) ppm.

MS (e.i., m/s %): 532 (M$^+$, 1), 501 (M$^+$—CH3O.8), 377 (M$^+$—CH$_3$(C$_6$H$_4$)SO$_2$, 94), 395 (M$^+$—CH$_3$O—CH$_3$(C$_6$H$_4$)SO$_2$H. 99) 317 (M$^+$—CH$_3$O—CH$_3$(C$_6$H$_4$)SO$_2$H—CO, 100), 196 (ArCO$^+$, 44), 182 (ArCH$_2$+, 22), 139 (CH$_3$(C$_6$H$_4$)SO$^+$, 11) 91 (CH$_3$(C$_6$H$_4$)$^+$, 16).

Elementary analysis for C$_{25}$H$_{28}$N$_2$O$_9$S:

Calculated: % C=56.38; % H=5.30: % N=5.26; % S=6.02

Found: % C=56.08; % H=5.45; N=5.13; % S=5.98

2) Methyl 2-[2-(4-methoxyphenl)-2-oxo-tosylethyl]-N-methoxymethyl-4-pyrrolcarboxylate A mixture of 1.42 g. of methyl 2-[2-hydroxy-2-(4-methoxyphenyl)-1-tosylethyl]-N-methoxymethyl-4-pyrrolcarboxylate and 1.7 g. of 2,3-dicyano-5,6-dichloro-p-benzoquinone in 70 mL of dry toluene is heated to reflux under argon for 12 hours.

Addition of a saturated solution of Na$_2$S$_2$O$_5$, followed by extraction dichloromethane, washing the organic solution with a saturated solution of Na$_2$S$_2$O$_5$, drying with sodium sulfate and concentrating the same, gives rise to an oil that can be purified by silica gel column chromatography (35×3 cm ø), by elution with ethyl acetate/hexane (1:1) to give rise to 1,27 g. of the desired ketone.

Yield: 90% m.p.: 108°–109° C.

IR (film, maximum δ): 1570, 1600, 1680. 1715 cm$^{-1}$

UV (ethanol, maximum λ): 294, 222 nm)

$^1$H-NMR (CDCl$_3$): 2.44 (s, 3H, ARCH$_3$), 3.26 (s, 3H, NCH$_2$OCH$_3$), 3.73 (s, 3H, CO$_2$CH$_3$), 3.85 (s, 3H, ArOCH$_3$), 4.97 (d, 1H, J=11.1 Hz, NCH$_2$OCH$_3$), 6.24 (d, 1H, J=11.1 Hz, NCH$_2$OCH$_3$), 6.39 (d, 1H, J=1.8 Hz, ArH), 6.54 (s, 1H, HCTs), 6.89 (d, 2H, J=9.0 Hz, ArH), 7.26 (d, 2H, J=8.3 Hz, ArH), 7.46 (d, 1 H, J=1.8 Hz, ArH), 7.52 (d, 2H, J=8.3 Hz, ArH), 7.96 (d, 2H, J=9.0 Hz, ArH) ppm.

MS (e.i., m/s, %) 471 (M$^+$, 3), 316 (M$^+$—TsH, 100), 135 (CH$_3$O(C$_6$H$_4$)CO$^+$, 49), 91 (CH$_3$C$_6$H$_4$+, 19).

3) Methyl 2-[2-(3,4,5-trimethoxyphenyl)-2-oxo-1-tosylethyl]-N-methoxymethyl-4-pyrrolcarboxylate A mixture of 2.65 g. of methyl 2-[2-hydroxy-2-(3,4,5-trimethoxyphenyl)-1-tosylethyl]-N-methoxymethyl-4-pyrrolcarboxylate and 3.95 g. of 2.3-dicyano-5,6-dichloro-p-benzoquinone in 90 mL of dry toluene is dried to reflux under argon for 9 hours.

The elimination of toluene gives rise to a dark residue that is dissolved in dichloromethane. The resulting solution is filtered, washed with an aqueous saturated Na$_2$SO3 solution and concentrated yielding a residue that is purified by silica gel column chromatography, by elution with dichloromethane-ethyl acetate (9:1), giving rise to 1.63 g. of the desired ketone.

Yield: 62%

$^1$H-NMR (CDCl$_3$): 2.46 (s, 3H, ARCH$_3$), 3.27 (s, 3H, NCH$_2$OCH$_3$), 3.75 (s, 3H, CO$_2$CH$_3$), 3.84 (s, 6H, ArOCH$_3$), 3.94 (2, 3H, ArOCH$_3$), 5.00 (d, 1H, J=11 Hz, NCH$_2$OCH$_3$), 6.26 (d, 1H, J=11 Hz, NCH$_2$OCH$_3$), 6.36 (d, 1H, J=1.7 Hz, ArH), 6.54 (s, 1H, HCTs), 7.27 (s, 2H, ArH), 7.28 (d, 2H, J=8.4 Hz, ArH), 7.48 (d, 1H, J=1 Hz, ArH), 7.5 (d, 2H, J=8.4 Hz, ArH) ppm.

EXAMPLE 3

1) Methyl 2-[2-acetoxy-2-(4-methoxycarbonyl-N-methoxymethyl-2-pyrril)-1-tosylethenyl]-N-methoxymethyl-4-pyrrolcarboxylate 4.4 mL of acetyl chloride are slowly added to a solution, magnetically stirred and kept at −40° C. under argon, of 4.67 g. of methyl 2-[2-(4-methoxycarbonyl-N-methoxymethyl-2-pirryl)-2-oxo-1-tosylethyl]-N-methoxymethyl-4-pyrrolcarboxylate and 12.1 mL of triethylamine in 60 mL of dry dichloromethane.

After 2.25 hours, 100 mL of hydrochloric acid 10% are added and extracted with dichloromethane. Drying with sodium sulfate and concentrating the organic phase yields an oil that is purified by silica gel column chromatography (18×3 cm ø), by elution with a hexane-ethyl acetate gradient of 40 to 60% in ethyl acetate. 4.96 g. of enol acetate.

Yield: 98% m.p. 59°–61° C. (Dichloromethane-ethyl acetate)

IR (film, maximum γ): 1720, 1785, 2880, 2960 cm$^{-1}$

UV (ethanol, maximum λ): 205, 302, 315 $_{shoulder}$nm $^1$H-MNR (CDCl$_3$): 2.32 (s, 3H, ArOCOCH$_3$), 2.42 (s, 3H, ARCH$_3$), 2.99 (s, 3H, NCH$_2$OCH$_3$), 3.20 (s, 3H, NCH$_2$OCH$_3$) 3.69 (s, 3H, ArCO$_2$CH$_3$), 3.76 (s, 3H, ArCO$_2$CH$_3$), 4.82 (d, 1H, J=10.6 Hz, ArCH$_2$OCH$_3$), 4.99 (d, 1H, J=10.6 Hz, ArCH$_2$OCH$_3$), 5.13 (d, 1H, J=10.6 Hz, ArCH$_2$OCH$_3$), 5.23 (d, 1H, J=10.6, ArCH$_2$OCH$_3$), 6.26 (d, 1H, J=1.8 Hz, ArH), 6.47 (d, 1H, J=1.8 Hz, ArH), 7.27 (d, 2H, J=8.1 Hz, ArH), 7.31 (d, 1H, J=1.7 Hz, ArH), 7.40 (d, 1H, J=1.8 Hz, ArH), 7.62 (d, 2H, J=8.3 Hz, ArH) ppm.

MS (e.i., m/s, %): 574 (M$^+$·, 4), 543 (M$^+$·—CH$_3$O. 7) 532 (M$^+$·—CH$_2$CO, 75), 500 (M$^+$·—CH$_3$OH—CH$_2$CO, 20), 377 (M$^+$·—CH$_2$CO—CH$_3$(C$_6$H$_4$)SO$_2$, 32), 345 (M$^+$·—CH$_3$OH—CH$_2$CO—CH$_3$(C$_6$H$_4$) SO$_2$, 90), 317 (M$^+$·—CH$_3$OH—CH$_2$CO—CH$_3$(C$_6$H$_4$)SO$_2$—CO, 54), 196 (ARCO$^+$, 41), 182 (ARCH$_2$+, 100), 139 (CH$_3$(C$_6$H$_4$)SO$^+$·, 24), 91 (CH$_3$(C$_6$H$_4$)+, 18.)

2) Methyl 2-[2-acetoxy-2-(4-methoxyphenyl)-1-tosylethenyl]-N-methoxymethyl-4-pyrrolcarboxylate 1.34 mL of acetyl chloride are slowly added on a solution, magnetically stirred and kept at −40° C. under argon, of 1.27 g. of methyl 2-[2-(4-methoxyphenyl)-2-oxo-1-tosylethyl]-N-methoxymethyl-4-pyrrolcarboxylate and 3.76 mL of tri-ethylamine in 60 mL of dry dichloromethane.

After 2 hours 20 mL of hydrochloric acid 10% are added and extracted with dichloromethane. Drying with sodium sulfate and concentration of the organic phase gives an oil that is purified by silica gel column chromatography (30×3 cm ø), by elution with hexane-ethyl acetate (1:1). 1.34 g. of enol acetate are obtained as the sole isomer.

Yield: 97% m.p. 152.5°–153.5° C.

IR (film, maximum δ): 1510, 1550, 1595, 1780, 2955 cm$^{-1}$

UV (ethanol, maximum λ): 298, 212 nm $^1$H-NMR (CDCl$_3$): 2.42 abd 2,43 (s, 3H, ArCH$_3$ and ArOCOCH$_3$), 3.00 (s, 3H, NCH$_2$OCH$_3$), 3.74 (s, 3H, ArCO$_2$CH$_3$), 3.79 (s, 3H, ArOCH$_3$), 4.64 (d, 1H, J=10.3 Hz, NCH$_2$OCH$_3$), 5.00 (d, 1H, J=10.3 Hz, NCH$_2$OCH$_3$), 6.44 (d, 1H, J=1.7 Hz, ArH), 6.69 (d, 2H, J=9.0 Hz, ArH), 7.12 (d, 2H, J=9.0 Hz, ArH), 7.28 (d, 2H, J=8.3 Hz, ArH), 7.54 (d, 1H, J=1.7 Hz, ArH), 7.68 (d, 1H, J=8.3 Hz, ArH)

MS (FAB, m/s, %): 514 (M+, 9), 471 (M+1—CH$_2$CO, 37) 440 (M+1—CH$_2$CO—CH$_2$OCH$_3$, 30) 135 (CH$_3$O(C$_6$H$_4$)$^+$, 100), 284 (M+1—CH$_2$CO—CH$_2$OCH$_3$—TsH, 33).

3) Methyl 2-[2-acetoxy-2-(3,4,5-trimethoxyphenyl)-1-tosylethenyl]-N-methoxymethyl-4-pyrrolcarboxilate 0.24 mL of acetyl chloride are slowly added to a solution, magnetically stirred and kept at −40° C. under argon, of 99 mg. of methyl 2-[2-(3,4,5-trimethoxyphenyl)-2-oxo-1-tosylethyl]-N-methoxymethyl-4-pyrrolcarboxylate and 0.24 mL of triethylamine in 5 mL of dry dichloromethane.

After 5.7 hours 5 mL of hydrochloric acid 10% are added and extracted with dichloromethane. Drying with sodium sulfate and concentration of the organic phase gives rise to an oil that is purified by silica gel column chromatography (15×1 cm ø), by elution with hexane-ethyl acetate (1:1). 101 mg. of enol acetate are obtained as a mixture of isomers in a ratio of 5:1.

Yield: 95%

IR (film, maximum δ): 1580. 1715, 1775. 2740, 2945, 2955, 3055, 3120 cm$^{-1}$

UV (ethanol, maximum λ): 304 nm.

$^1$H-NMR (CDCl$_3$) (majority isomer) 2.43 and 2.42 (s, 3H, ArCH$_3$ and ArOCOCH$_3$), 3.12 (s, 3H, NCH$_2$OCH$_3$), 3.79–374 (singlets, 6H, ArOCH$_3$ and ArOCH$_3$), 4.94 (d, 1H, J=10.1 Hz, NCH$_2$OCH$_3$), 5.12 (d, 1H, J=10.5 Hz, NCH$_2$OCH$_3$), 6.39 (d, 1H, J=1.7 Hz, ArH), 7.27 (s, 2H, ArH), 7.32 (d, 2H, J=8.4 Hz, ArH), 7.48 (d, 1H, J=1.8 Hz, ArH), 7.70 (d, 2H, J=8.3 Hz, ArH) ppm.

EXAMPLE 4

1) Dimethyl 5-acetoxy-3,6-bis(methoxymethyl)-4-tosyl-3,6-dihydropyrrol[3,2-e]indol-1,8-dicarboxylate An aerated solution of 2.30 g. of methyl 2-[2-acetoxy-2-(4-methoxycarbonyl-N-methoxymethyl-2-pirryl)-1-tosylethenyl]-N-methoxymethyl-4-pyrrolcarboxylate and 160 mg. of iodine in 225 mL of ethanol, introduced in a photochemical Pyrex glass reactor is irradiated for 3.5 hours with ultraviolet light produced by a Hanowia 400 W lamp.

Addition of an aqueous saturated solution of Na$_2$S$_2$O$_5$ until the color due to the iodine disappears, followed by elimination of the ethanol under reduced pressure, extraction with dichloromethane, drying of the organic phase with sodium sulfate and elimination of the solvent, gives rise to a residue that is purified by silica gel column chromatography (19×2 cm ø), by elution with hexane-ethyl acetate (1:1) to give 2.18 g. of the desired pyrrolindol.

Yield: 95% m.p.: 128°–130° C. (hexane-ethyl acetate)

IR (film, maximum δ): 1720, 1790, 2950 cm$^{-1}$

UV (ethanol, maximum λ): 202, 215, 237, 264, 326 nm $^1$H-NMR (CDCl$_3$): 2.26 (s, 3H, ArOCOCH$_3$), 2.35 (s, 3H, ARCH$_3$). 2.96 (s, 3H, NCH$_2$OCH$_3$), 3.14 (s, 3H, NCH$_2$OCH$_3$), 3.82 (s, 3H, ArCO$_2$CH$_3$), 3.83 (s, 3H, ArCO$_2$CH$_3$), 4.97 (d, 1H, J=10.9 Hz, NCH$_2$OCH$_3$), 5.79 (m, 3H, NCH$_2$OCH$_3$), 7.18 (d, 2H, J=8.1 Hz, ArH), 7.55 (d, 2H, J=8.3 Hz, ArH), (s, 1H, ArH), 7.96 (s, 1H, ArH) ppm.

MS (e.i., m/s, %): 572 (M$^+$·—CH$_2$O, 100), 498 (M$^+$·—CH$_2$O—CH$_3$OH, 49), 433 (M$^+$·—CH$_3$(C$_6$H$_4$)SO, 33), 402 (M$^+$·—CH$_3$ (C$_6$H$_4$)SO—CH$_3$O, 67), 375 (M$^+$·—CH$_2$CO—CH$_3$(C$_6$H$_4$)SO$_2$, 67), 343 (M$^+$·CH$_2$CO—CH$_3$(C$_6$H$_4$)SO$_2$—CH$_3$OH. 38), 139 (CH$_3$(C$_6$H$_4$)SO$^+$, 29), 91 (CH$_3$(C$_6$H$_4$)$^+$, 23).

Elementary analysis for C$_{27}$H$_{28}$N$_2$O$_{10}$S:

Calculated: % C=56.64; % H=4.93; % H=4.89; % S=5.60

Found: % C=56.89; % H=5.05; % N=5.01; % S=5.66

2) Methyl 5-acetoxy-8-methoxy-N-methoxymethyl-4-tosylbenzo[e]indol-1-carboxylate An aerated solution of 560 mg. of methyl 2-[2-acetoxy-2-(4-methoxyphenyl)-1-tosylethenyl]-N-methoxymethyl-4-pyrrolcarboxylate and 40 mg. of iodine in 100 mL of ethanol introduced in a photochemical Pyrex glass reactor, is irradiated for 17 hours with ultraviolet light produced by a Hanowia 400 W lamp.

Addition of an aqueous saturated solution of Na$_2$S$_2$O$_5$ until the color due to the iodine disappears, followed by elimination of the ethanol under reduced pressure, extraction with dichloromethane, drying of the organic phase with sodium sulfate and elimination of the solvent gives rise to a residue that is purified by silica gel column chromatography (23×1 cm ø), by elution with hexane-ethyl acetate (1:1) to give 457 mg. of the desired pyrrolindol.

Yield: 82% m.p.: 163°–164° C.

IR (KBr, maximum δ): 1510, 1620, 1710, 1780, 2950, 3120 cm$^{-1}$

UV (ethanol, maximum λ): 216, 272, 326 nm $^1$H-NMR(CDCl$_3$): 2.37 (s, 3H, ARCH$_3$), 2.39 (s, 3H, ArOCOCH$_3$), 2.95 (s, 3H, ArCH$_2$OCH$_3$), 3.95 (s, 3H, ArCO$_2$ CH$_3$), 4.06 (s, 3H, ArCO$_2$CH$_3$) 5.86 (s, 2H, ArCH$_2$OCH$_3$), 7.13 (dd, 1 H, J=2.5 and 9.2 Hz, ArH), 7.2 (d, 2H, J=8.2 Hz, ArH), 7.59 (d, 2H, J=8.2 Hz, ArH), 7.60 (s, 1H, ArH), 8,24. (s, 1H, ArH), 9.42 (d, 1H, J=2.5 Hz, ArH) ppm MS (e.i., m/s, %): 511 (M⁺·, 11), 469 (M⁺·—CH₂CO, 100), 437 (M⁺·—CH₂CO—CH₃OH, 35), 315 (M⁺·—CH₂CO—Ts. 40), 139 (CH₃(C₆H₄)SO⁺·, 26), 91 (CH₃(C₆H₄)⁺·, 12).

3) Methyl 5-acetoxy-7,8,9-trimethoxy-N-methoxymethyl-4-tosylbenzo[e]indol-1-carboxylate An aerated solution of 101 mg. of methyl 2-[2-acetoxy-2-(3,4,5-trimethoxyphenyl-1-tosylethenyl]-N-methoxymethyl-4-pyrrolcarboxylate and 9 mg. of iodine in 30 mL of ethanol, introduced in a photochemical Pyrex glass reaction, is irradiated for 2.6 hours with ultraviolet light produced by a Hanowia 400 W lamp.

Addition of an aqueous saturated solution of Na₂S₂O₅ until the color due to the iodine disappears, followed by elimination of the ethanol under reduced pressure, extraction with dichloromethane, drying of the organic phase with sodium sulfate and elimination of the solvent, gives rise to a residue that is purified by silica gel column chromatography, by elution with a dichloromethane-ethyl acetate gradient, increasing the proportion of ethyl acetate from 0 to 10%, to give 32 mg. of the desired pyrrolindol.

Yield: 32%

UV (ethanol, maximum λ): 228, 256, 336 nm.

¹H-NMR (CDCl₃): 2.39 (s, 6H, NCH₂OCH₃ and ARCH₃), 2.95 (s, 3H, ArOCOCH₃), 3.73 (s, 3H, ArOCH₃), 3.84 (s, 3H, ArOCH₃), 3.90 (s, 3H, ArCO₂CH₃), 4.06 (s, 3H, ArOCH₃), 5.84 (s, 2H, NCH₂OCH₃), 6.79 (s, 1H, ArH), 7.25 (d, 2H, J=8.5 Hz, ArH), 7.67 (d, 2H, J=8.4 Hz, ArH), 7.74 (s, 1H, ArH) ppm.

We claim:

1. New areno[e]indols useful as intermediates in the synthesis of products with antitumor activity of formula:

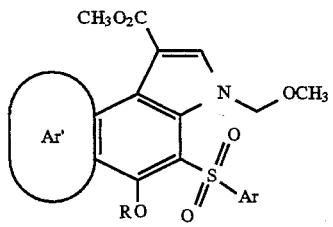
(I)

wherein:
—Ar represents phenyl or substituted phenyl
—Ar' represents a condensed radical of formulae:

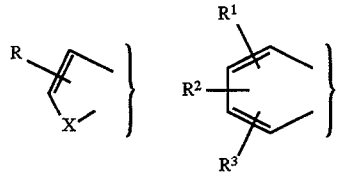

wherein R, R¹, R², R³ can represent a hydrogen, a halogen, a linear or branched alkyl, alkenyl or alkynyl radical, a formyl, acyl, carboxy, alkoxycarbonyl, aminocarbonyl, alkylaminocarbonyl, dialkylaminocarbonyl, cyano, hydroxy, alkoxy, amino, alkylamino, dialkylamino, acylamino or nitro radical; and X represents oxygen, sulfur or substituted or unsubstituted nitrogen.

2. New areno[e]indols, according to claim 1, which have the following structural formula:

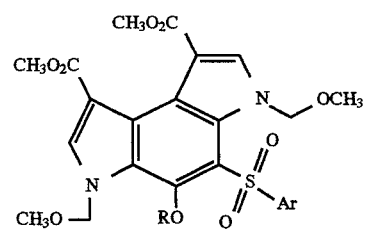

wherein R represents an acyl group of 2 to 5 linear or branched chain carbon atoms and Ar represents phenyl or substituted phenyl.

3. New areno[e]indols, according to claim 1, which have the following structural formula:

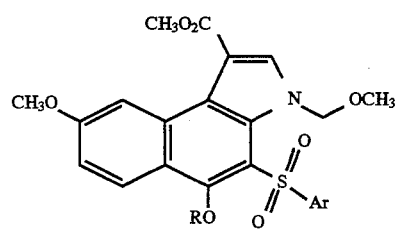

wherein R represents an acyl group of 2 to 5 linear or branched chain carbon atoms and Ar represents phenyl or substituted phenyl.

4. New areno[e]indols, according to claim 1, which have the following structural formula:

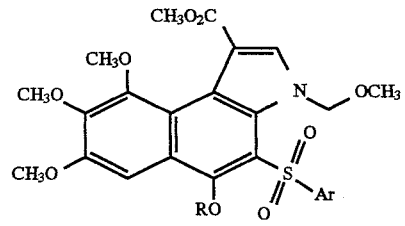

wherein R represents an acyl group of 2 to 5 linear or branched chain carbon atoms and Ar represents phenyl or substituted phenyl.

* * * * *